(12) United States Patent
Papay

(10) Patent No.: US 8,512,715 B2
(45) Date of Patent: Aug. 20, 2013

(54) APPARATUS AND METHOD FOR TREATING A NEUROMUSCULAR DEFECT

(75) Inventor: Francis A. Papay, Westlake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 580 days.

(21) Appl. No.: 12/541,221

(22) Filed: Aug. 14, 2009

(65) Prior Publication Data
US 2010/0143413 A1 Jun. 10, 2010

Related U.S. Application Data

(60) Provisional application No. 61/089,015, filed on Aug. 14, 2008.

(51) Int. Cl.
*A61K 39/08* (2006.01)

(52) U.S. Cl.
USPC ...................................... 424/239.1

(58) Field of Classification Search
None
See application file for complete search history.

(56) References Cited

U.S. PATENT DOCUMENTS

| | | | |
|---|---|---|---|
| 5,714,468 A | | 2/1998 | Binder |
| 5,730,719 A | * | 3/1998 | Edwards ........................ 604/22 |
| 6,024,733 A | * | 2/2000 | Eggers et al. ................. 604/500 |
| 6,139,545 A | * | 10/2000 | Utley et al. ..................... 606/34 |
| 6,896,886 B2 | * | 5/2005 | Aoki et al. ................ 424/184.1 |
| 7,326,207 B2 | * | 2/2008 | Edwards ........................ 606/41 |
| 7,331,956 B2 | * | 2/2008 | Hovda et al. .................... 606/32 |
| 7,470,236 B1 | * | 12/2008 | Kelleher et al. ............... 600/554 |
| 8,034,051 B2 | * | 10/2011 | Martin et al. ................... 606/41 |
| 2001/0047167 A1 | * | 11/2001 | Heggeness ..................... 606/41 |
| 2004/0186468 A1 | * | 9/2004 | Edwards ........................ 606/41 |
| 2004/0260358 A1 | * | 12/2004 | Vaughan et al. ................ 607/48 |
| 2005/0084504 A1 | | 4/2005 | Aoki et al. |
| 2005/0183732 A1 | * | 8/2005 | Edwards ........................ 128/898 |
| 2006/0015151 A1 | * | 1/2006 | Aldrich ........................... 607/40 |
| 2007/0010809 A1 | * | 1/2007 | Hovda et al. .................... 606/41 |
| 2007/0021803 A1 | * | 1/2007 | Deem et al. .................... 607/46 |
| 2007/0055179 A1 | * | 3/2007 | Deem et al. ...................... 601/2 |

(Continued)

FOREIGN PATENT DOCUMENTS

WO   WO 01/12089 A1   2/2001

OTHER PUBLICATIONS

Barwood et al (Developmental Medicine & Child Neurology, 2000, 42, 116-121).*
Ferrante et al (Anesth. Analges;1996;82,91-97).*
Robert Bohinski, MD et al, pp. 1-6, Feb. 2010, Degenerative disc disease (spondylosis) overview, on-line source spine-health or spineuniverse websites.*

*Primary Examiner* — Albert Navarro
*Assistant Examiner* — Ginny Portner
(74) *Attorney, Agent, or Firm* — Tarolli, Sundheim, Covell & Tummino LLP

(57) ABSTRACT

A method is provided for treating a neuromuscular defect in a subject. One step of the method includes locating a target nerve. After locating the target nerve, a treatment probe is provided. The treatment probe includes an elongated body member having a proximal end portion and a distal end portion. The distal end portion includes an energy delivery mechanism for stimulating or ablating the target nerve, a monitoring mechanism, and a fluid aspiration/delivery mechanism. Next, the target nerve is verified as an appropriate target for ablation by stimulating and then monitoring the target nerve via the energy delivery mechanism and the monitoring mechanism, respectively. After verifying the target nerve, a tumescent fluid is injected into the tissue surrounding the target nerve. An electric current is then delivered to the energy delivery mechanism to substantially ablate the target nerve.

8 Claims, 9 Drawing Sheets

(56) References Cited

U.S. PATENT DOCUMENTS

Figure 1:
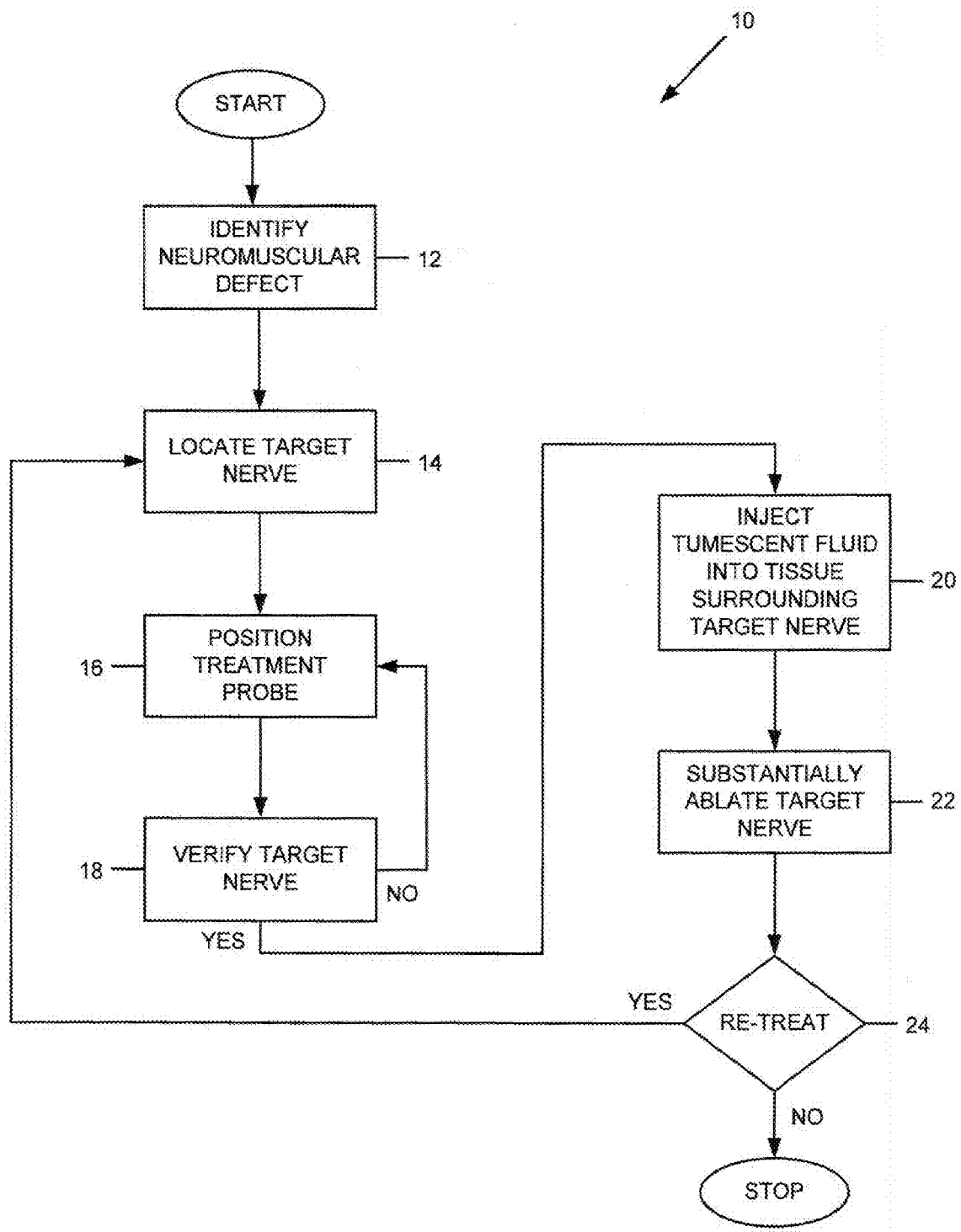

| | | |
|---|---|---|
| 2007/0129714 A1 | 6/2007 | Elkins et al. |
| 2007/0167943 A1 | 7/2007 | Janssen et al. |
| 2007/0255342 A1 | 11/2007 | Laufer |
| 2007/0293782 A1* | 12/2007 | Marino .................. 600/546 |
| 2008/0069841 A1 | 3/2008 | Panjwani et al. |
| 2010/0010484 A1* | 1/2010 | Mehta et al. .............. 606/33 |
| 2010/0286684 A1* | 11/2010 | Hata et al. ................ 606/33 |

* cited by examiner

APPARATUS AND METHOD FOR TREATING A NEUROMUSCULAR DEFECT

RELATED APPLICATION

This application claims priority from U.S. Provisional Patent Application Ser. No. 61/089,015, filed Aug. 14, 2008, the subject matter of which is incorporated hereby incorporated by reference in its entirety.

TECHNICAL FIELD

The present invention relates generally to an apparatus and method for neuromodulation, and more particularly to an apparatus and method for interrupting nerve conduction through a target nerve to treat a neuromuscular defect.

BACKGROUND OF THE INVENTION

The human nervous system senses current information and conditions, which it then sends to various muscles to respond. As one example, consider the facial and neck nerves. These motor nerves control the muscles of facial expression and, thus, an individual's outward manifestations of well being and emotion. Neuromuscular defects can disrupt this information exchange and lead to undesired muscle responses.

The involuntary contraction of facial or neck muscles (also known as dystonias) can distort an individual's facial expressions and garble the outward appearance of the individual's feeling of well being and emotional state. For example, one type of dystonia, called belpharospasm, creates uncontrolled blinking and spasms in the eyelids. Another form of dystonia causes uncontrolled grimacing. Dystonias can also affect neck muscles. For example, one form of dystonia, called torticollis, causes uncontrolled contraction of the neck muscles.

Apart from these hyperfunctional disorders, normal contraction of facial and neck muscles (e.g., by frowning or squinting) can form permanent furrows or bands in the skin over time. These furrows or bands can present an aesthetically displeasing cosmetic appearance, and exposure to the sun can accelerate this undesired wrinkling process. As a more specific example, the facial muscle corrugator supercilii draws the eyebrows downward and inward, producing vertical wrinkles of the forehead (also called glabellar frown lines). For this reason, the corrugator supercilii is known as the frowning muscle and has been called the principal agent in the expression of suffering. Dystonias affecting the corrugator supercilii can lead to an unfortunate, continuous frowning expression, as well as the formation of hyperfunctional frown lines and wrinkles in the face.

A surgical forehead lift procedure is one therapeutic modality often used to remove glabellar frown lines. The forehead lift requires a large incision that extends from ear to ear over the top of the forehead. This surgically invasive procedure imposes the risk of bleeding and creates a large skin flap that reduces blood supply to the skin. Numbness of sensory nerves in the face, such as the supraorbital nerve can also result.

A less invasive therapeutic modality is the administration of invertebrate exotoxins. For example, injection of the serotype A of the *Botulinum* toxin produces a flaccid paralysis of the corrugator supercilii. Tests have demonstrated that *Botulinum* toxin A may be administered into the musculature of the face without toxic effect to produce localized muscle relaxation for a period of about six months. The desired removal of hyperfunctional frowning lines is temporary, and repeated treatments are needed about every 3 to 6 months.

Another form of treatment, disclosed in U.S. Pat. No. 5,370,642 to Keller, uses laser energy to eliminate glabellar frown lines and forehead wrinkles. The laser energy is used to resect large sections of the corrugator supercilii (as well as other facial muscles) and thereby inactivate the muscles. Like the surgical forehead lift, numbness of the supraorbital nerve and other sensory nerves in the face can result.

SUMMARY OF THE INVENTION

According to one aspect of the present invention, a method is provided for treating a neuromuscular defect in a subject. One step of the method includes locating a target nerve. After locating the target nerve, a treatment probe is provided. The treatment probe comprises an elongated body member having a proximal end portion and a distal end portion. The distal end portion includes an energy delivery mechanism for stimulating or ablating the target nerve, a monitoring mechanism, and a fluid aspiration/delivery mechanism. Next, the target nerve is verified as an appropriate target for ablation by stimulating and then monitoring the target nerve via the energy delivery mechanism and the monitoring mechanism, respectively. After verifying the target nerve, a tumescent fluid is injected into the tissue surrounding the target nerve. An electric current is then delivered to the energy delivery mechanism to substantially ablate the target nerve.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a process flow diagram illustrating a method for treating a neuromuscular defect in a subject according to the present invention;

FIG. 2 is a schematic illustration of a subject's orbital region showing uncontrolled blinking or blepharospasm;

FIG. 3 is an anterior view of the right side of the face showing the superficial facial and neck muscles and the branches of the facial nerves that control the facial and neck muscles;

FIG. 4A is a perspective view of a treatment probe constructed in accordance with the present invention;

FIG. 4B is an exploded perspective view showing a distal end portion of the treatment probe in FIG. 4A;

FIG. 5 is a perspective view showing the distal end portion of the treatment probe in FIG. 4A being positioned about a target nerve;

FIG. 6 is a perspective view showing the treatment probe in FIG. 5 being used to deliver a tumescent fluid to the tissue surrounding the target nerve;

FIG. 7A is a perspective view showing a neuromuscular junction located between a target nerve and a muscle;

FIG. 7B is a perspective view showing the distal end portion of the treatment probe in FIG. 4B being used to substantially ablate the target nerve; and FIG. 8 is a schematic illustration showing the subject in FIG. 2 after being treated for blepharospasm by the present invention.

DETAILED DESCRIPTION

The present invention relates generally to an apparatus and method for neuromodulation, and more particularly to an apparatus and method for interrupting nerve conduction through a target nerve to treat a neuromuscular defect. As representative of the present invention, FIG. 1 illustrates a method 10 for treating a neuromuscular defect in a subject. Although the present invention is described primarily in terms of treating cosmetic conditions affecting the face and neck, such as involuntary contraction of facial or neck muscles or the appearance of lines and wrinkles in the face or neck, it should be appreciated that other neuromuscular defects, such as headaches and neuromuscular pain can also be treated by the present invention.

Unless otherwise defined, all technical terms used herein have the same meaning as commonly understood by one of ordinary skill in the art to which the present invention pertains.

In the context of the present invention, the terms "modulate" or "modulating" can refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, thermal, ultrasonic, optical or chemical, or a combination of two or more of these. The terms "modulate" or "modulating" can also be used to refer to a masking, altering, or overriding of neuronal activity.

Figure 3:
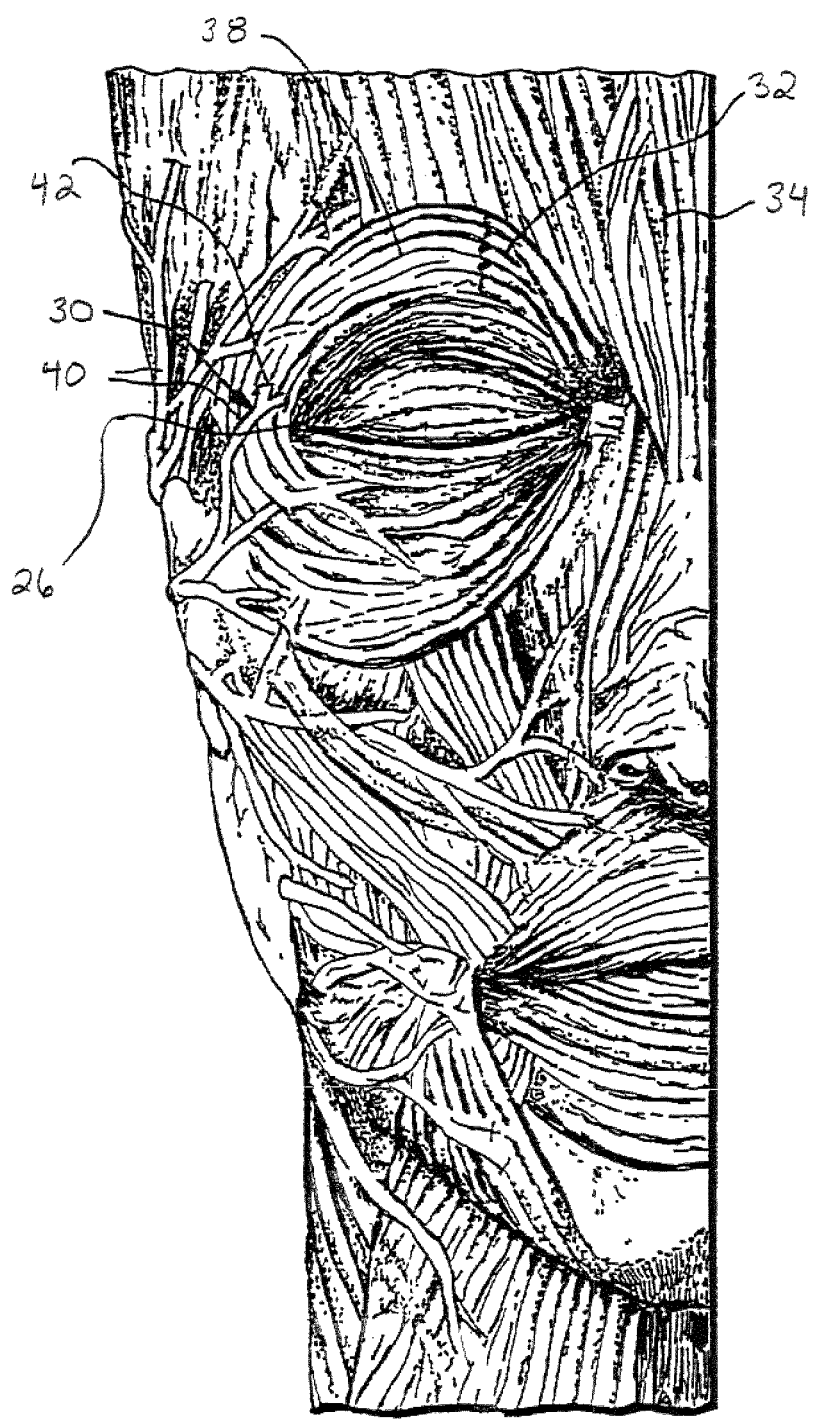

As used herein, the term "target nerve" can refer to any portion of a human (or other mammalian) nervous system that has been identified to benefit from receiving electric current. Non-limiting examples of target nerves can include the facial nerve and any one of its branches, such as the temporal branch, the zygomatic branch, the buccal branch, the marginal mandibular branch, and the cervical branch. Other examples of target nerves are illustrated in FIG. 3 and described in more detail below.

As used herein, the term "substantially ablate" can refer to damage caused to a target nerve that results in partial or complete nervous tissue or nerve cell necrosis. The term can also refer to nervous tissue or nerve cell damage that falls short of complete ablation, e.g., some level of agitation or damage that is imparted to the nervous tissue or nerve cell to inure a desired change in the cellular makeup and/or electrical activity of the tissue/cell, rather than necrosis of the tissue/cell.

As used herein, the term "subject" can refer to any warm-blooded organism including, but not limited to, human beings, pigs, rats, mice, dogs, goats, sheep, horses, monkeys, apes, rabbits, cattle, etc.

FIG. 1 is a process flow diagram illustrating one aspect of the present invention. In FIG. 1, a method 10 is provided for treating a neuromuscular defect in a subject. At 12, one step of the method 10 includes identifying a neuromuscular defect in a subject. Generally, the neuromuscular defect can include any disease, disorder, or condition that adversely affects both nervous elements (e.g., brain, spinal cord, peripheral nerve) and muscle (e.g., striated or smooth). Non-limiting examples of neuromuscular defects can include cosmetic defects, neurological movement disorders, neuromuscular pain, and headaches.

Non-limiting examples of cosmetic defects can include frown lines, lines or wrinkles between the eyes 26 (FIG. 2), crow's feet, horizontal lines in the forehead and neck, wrinkles around the mouth and chin, skin furrows, contractions in the face and neck, spasms in the face or neck, and neck bands.

Neurological movement disorders can include any neurological disease or condition that affects the speed, fluency, quality, and/or ease of movement in a subject. For example, abnormal fluency or speed of movement (dyskinesia) may involve excessive or involuntary movement (hyperkinesia) or slowed or absent voluntary movement (hypokinesia). Examples of neurological movement disorders can include, but are not limited to, dystonias, torticollis, bleharospasm, and uncontrolled grimacing.

Non-limiting examples of neuromuscular pain can include myofascial pain, fibromyalgia, TMJ pain, carpal tunnel syndrome, pain associated with muscular dystrophy, orofacial pain, chronic head and neck pain, and pain associated with herniated and/or bulging or ruptured vertebral discs. Myofascial pain can involve any one or combination of nerves that supply the face or, alternatively, indirect (referred) pain from other structures in the head, e.g., blood vessels. Myofascial pain may be related to headache (e.g., migraine), muscular syndromes, such as TMJ, and herpetic or rheumatic disease or injury.

Non-limiting examples of headaches can include migraines, tension headaches, cluster headaches, trigeminal neuralgia, secondary headaches, and miscellaneous-type headaches. Migraines can include intense and disabling episodic headaches typically characterized by severe pain in one or both sides of the head. For example, migraines can include migraine without aura, migraine with aura, and migraine with aura but without headache. Cluster headaches can include extremely painful and debilitating headaches that occur in groups or clusters. For example, cluster headaches can include cluster-type headaches, histamine headaches, histamine cephalalgia, Raedar's syndrome, and sphenopalatine neuralgia.

Figure 2:
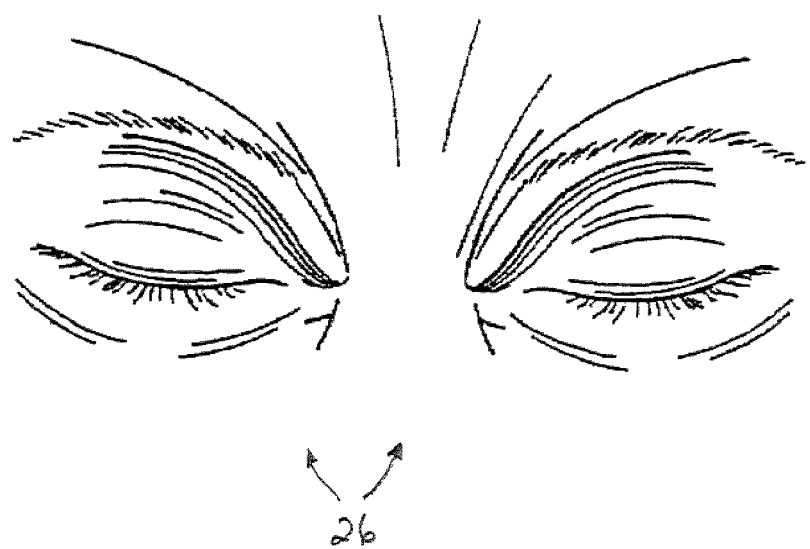

To identify the neuromuscular defect, a subject is monitored for one or more observable clinical symptoms associated with a particular neuromuscular defect. As shown in FIG. 2, for example, a subject suffering from blepharospasm may exhibit involuntary and sustained muscle contractions of the muscles around the eyes 26. Alternatively, symptoms associated with a particular neuromuscular defect may not be clinically observable. In this case, the subject may be asked to report his or her symptom(s) associated with the particular neuromuscular defect. For example, the subject may report the sensation of facial or head pain associated with a headache.

After the neuromuscular defect has been identified, a target nerve is located at 14. Generally, the target nerve can include any portion of a subject's nervous system that has been identified to benefit from receiving electric current based on the identified neuromuscular defect. Examples of target nerves in the face of a subject, as well as the muscles innervated by the target nerves are illustrated in FIG. 3. It should be appreciated, however, that other target nerves, such as those of the peripheral nervous system may also be targeted by the method of the present invention.

Referring to FIG. 3, the facial nerve 30 is the motor nerve that controls a significant portion of the muscles responsible for facial expressions. The branches of the facial nerve 30 pass around and through superficial facial and neck muscles to control the corrugator supercilii muscle 32, the procerus muscle 34, and the platysma myoides muscle 36, among many others. The facial nerve 30 is the seventh cranial nerve, which is part of the peripheral nervous system of the body. Disorders or defects in facial nerve 30 function can cause various cosmetic defects, such as blepharospasm. Thus, the facial nerve 30 and/or one of its branches can be an appropriate target nerve for treating a subject suffering from blepharospasm.

The corrugator supercilii 32 is a small and narrow pyramidal muscle. The corrugator supercilii 32 is located at the inner extremity of the eyebrow beneath the orbicularis palpebrarum muscle 38. As FIG. 3 shows, the temporal branch 40 of the facial nerve 30 provides additional nerve branches 42 to the corrugator supercilii muscle 32. The corrugator supercilii muscle 32 is called the "frowning muscle" because it draws the eyebrows downward and inward, producing vertical wrinkles in the forehead and in the space between the eyebrows.

The procerus 34 is a small, pyramidal band of muscles located over the nasal bone between the eyebrows. The zygomatico-buccal branch (not shown in detail) of the facial nerve 30 supplies the procerus muscle 34. The procerus muscle 34 draws down the inner angle of the eyebrows and produces transverse wrinkles over the bridge of the nose.

The platysma myoides 36 is a broad, thin plane of muscular fibers located immediately beneath the superficial fascia on each side of the neck. The cervical branch (not shown in detail) of the facial nerve 30 supplies the platysma myoides muscle 36. The platysma myoides muscle 36 produces a wrinkling of the surface of the skin of the neck, in an oblique direction, when the entire muscle is brought into action. It also serves to draw down the lower lip and angle of the mouth on each side.

A neuromuscular defect can lead to uncontrolled contraction of one or more of the corrugator supercilii 32, the procerus 34, and the platysma myoides 36 muscles. Uncontrolled contraction of the corrugator supercilii muscle 32 or the procerus muscle 34, for example, can continuously contract the brow, giving the outward appearance of displeasure or disapproval even in the absence of the corresponding emotional state. Likewise, uncontrolled contraction of the platysma myoides muscle 36 (called torticollis) can lead to sudden neck movement. Repeated normal contraction of the platysma myoides muscles 36 can also lead to the formation of aesthetically displeasing bands in the skin area below the neck over time. Even without hyperfunctional dysfunction, normal contraction of these muscles can, over time, cause aesthetically displeasing frown lines or furrows in the forehead or in the space between the eyebrows. Additionally, exposure to the sun can accelerate this wrinkling process.

Figure 4A:
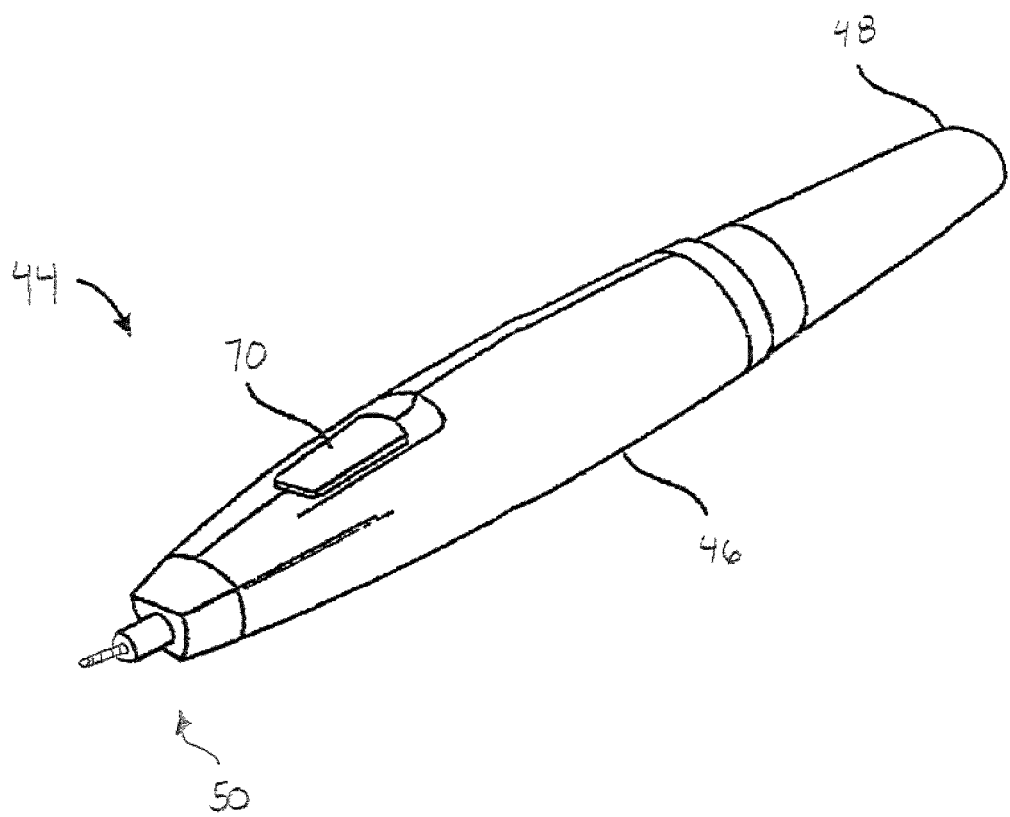
Figure 4B:
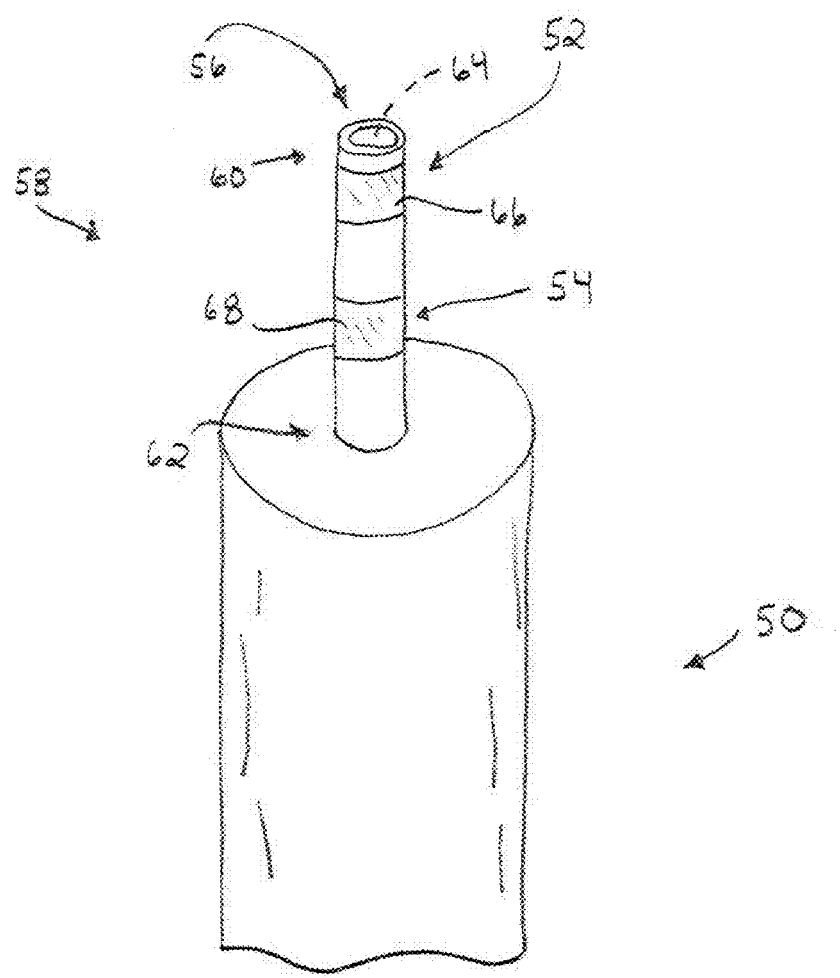

At 14, a treatment probe 44 (FIG. 4A) is used to verify that the target nerve is an appropriate target for ablation. As shown in FIG. 4A, the treatment probe 44 comprises an elongated body member 46 having a proximal end portion 48 and a distal end portion 50. The distal end portion 50 includes an energy delivery mechanism 52 (FIG. 4B) for delivering electric current to a target nerve. As shown in FIG. 4B, the distal end portion 50 also includes a monitoring mechanism 54 for monitoring the electrical activity of a target nerve and a fluid aspiration/delivery mechanism 56.

The energy delivery mechanism 52 and the monitoring mechanism 54 can be included as part of a hollow post member 58 located at the distal end portion 50 of the treatment probe 44. The post member 58 can have a distal end portion 60, a proximal end portion 62, and a channel 64 extending between the end portions. The proximal end portion 62 can be integrally formed with the elongated body member 46. Although not shown in FIG. 4B, the distal end portion 60 of the post member 58 can include a sharpened tip for penetrating tissue.

The energy delivery mechanism 52 can comprise a cuff or ring-shaped electrode 66 disposed on the distal end portion 60 of the post member 58. The electrode 66 can be made of any electrically-conductive material, such as platinum or platinum-iridium. It will be appreciated that any number of electrodes 66 may be operably disposed on the post member 58 and, further, that the electrode(s) can have any desired shape, such as a rectangular or ovoid shape.

The monitoring mechanism 54 can comprise a sensor 68 operably disposed on the post member 58. As shown in FIG. 4B, the sensor 68 is located proximal to the energy delivery mechanism 52; however, it should be appreciated that the sensor may alternatively be located distal to the energy delivery mechanism. The sensor 68 is capable of monitoring a desired metabolic parameter (e.g., electrical activity) associated with a nerve, nervous tissue, and/or muscle function. For example, the monitoring mechanism 54 can include at least one electromyographic (EMG) electrode capable of receiving a signal from a target nerve or muscle tissue when the electrode is placed in contact with the target nerve or muscle tissue. As explained in more detail below, the monitoring mechanism 54 can be used to verify that a target nerve is an appropriate target for ablation.

Referring again to FIG. 4B, the fluid aspiration/delivery mechanism 56 comprises the channel 64 extending between the distal and proximal end portions 60 and 62 of the post member 58. The fluid aspiration/delivery mechanism 56 can be used to selectively deliver a fluid or solution to a target nerve and/or the tissue surrounding the target nerve. For example, the fluid aspiration/delivery mechanism 56 can be used to deliver a tumescent fluid (described below) to the tissue surrounding a target nerve. Additionally, the fluid aspiration/delivery mechanism 56 can be used to aspirate or remove fluid from the tissue at (or surrounding) a target nerve.

A power button 70 (FIG. 4A) is operably disposed on the elongated body member 46 of the treatment probe 44, and can be used to selectively control the energy delivery mechanism 52, the monitoring mechanism 54, and the fluid aspiration/delivery mechanism 56. For example, the power button 70 can be used to control delivery of electric current to the energy delivery mechanism 52. Electrical energy can be delivered via a power source (not shown), such as a battery contained within the treatment probe 44. Alternatively, electrical energy can be delivered via a power source externally coupled to the treatment probe 44. For example, the power source can be electrically connected to the proximal end portion 48 of the treatment probe 44 using an insulated electrical lead or wire (not shown). The power source can comprise any device capable of generating electrical energy, such as high frequency ultrasound, high energy radiowaves, high frequency electrical stimulation, and laser energy.

At 16, the distal end portion 50 of the treatment probe 44 is positioned at or near a target nerve. Any one or combination of approaches can be used to access the target nerve with the treatment probe 44. For example, the post member 58 can be inserted directly through the skin adjacent a target nerve or, alternatively, an incision 72 (FIG. 5) can be made in the skin adjacent the target nerve. In a subject suffering from blepharospasm, for example, an incision 72 can be made near the right corner of a subject's eye 26 using a scalpel (not shown). In this case, the incision 72 should be made so that a portion of the facial nerve 30 and/or one of its branches is sufficiently exposed to facilitate accurate placement of the treatment probe 44.

Figure 5:
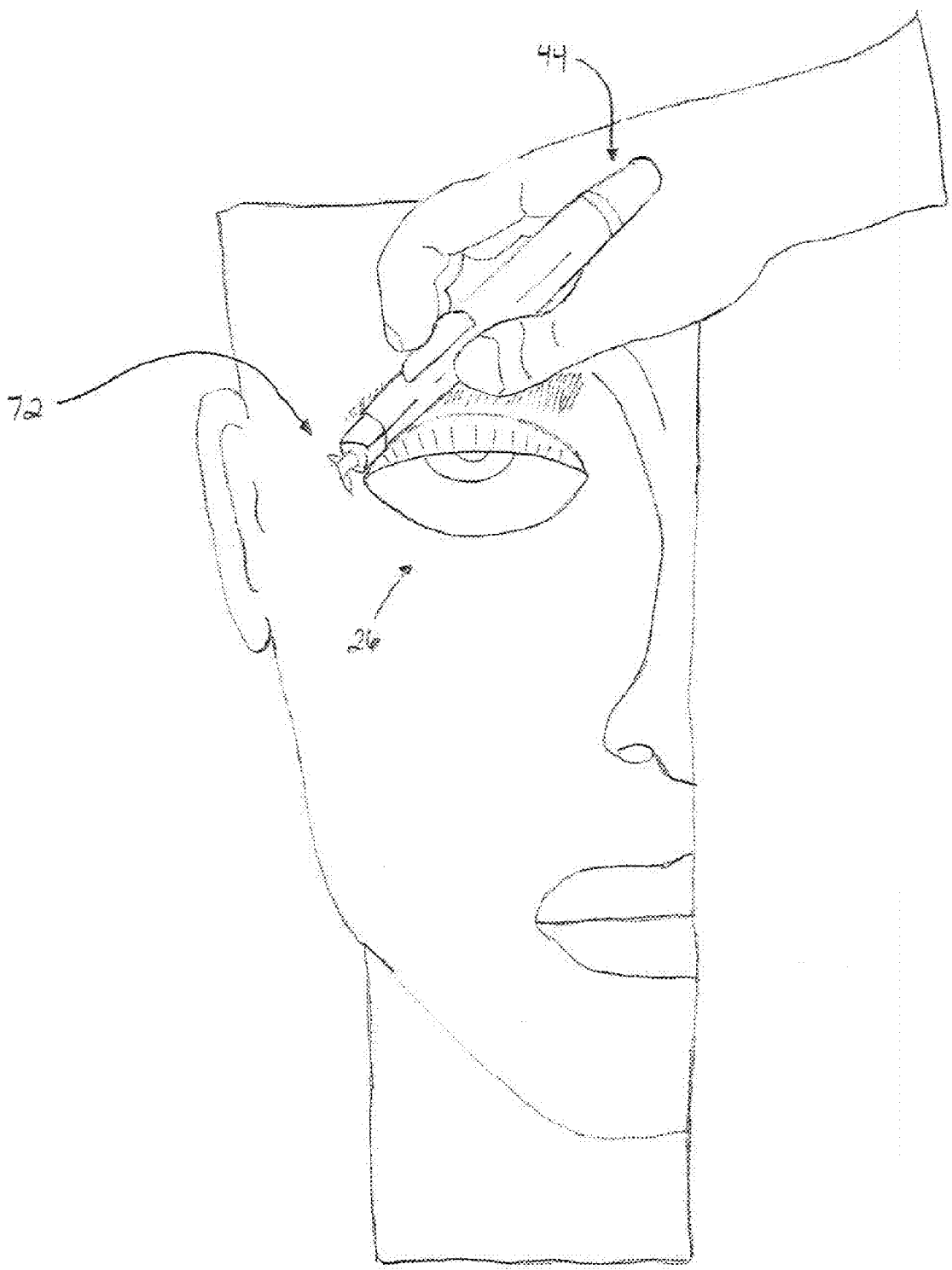

Next, the distal end portion 50 of the treatment probe 44 is urged through the incision 72 so that the distal end portion 60 of the post member 58 is in electrical contact with the target nerve. By "electrical contact" it is meant that when electric current is delivered to the energy delivery mechanism 52, depolrization of at least one neuron comprising the target nerve is elicited. As shown in FIG. 5, for example, the distal end portion 50 of the treatment probe 44 can be inserted into the incision 72 so that the energy delivery mechanism 52 is adjacent a portion of the facial nerve 30 and/or one of its branches. The position of the energy delivery mechanism 52 relative to the target nerve can be adjusted using the monitoring mechanism 54 during placement of the treatment probe 44. For example, the position of the energy delivery mechanism 52 can be adjusted based on sensed electrical patterns in the target nerve and/or tissue surrounding the target nerve using EMG mapping.

Following placement of the treatment probe 44, a determination is made as to whether the target nerve is appropriate for ablation at 18. To verify whether the target nerve is appropriate for ablation, electric current is delivered to the energy delivery mechanism 52. Electric current can be delivered to the energy delivery mechanism 52 continuously, periodically, episodically, or a combination thereof. For example, electric current can be delivered in a unipolar, bipolar, and/or multipolar sequence or, alternatively, via a sequential wave, charge-balanced biphasic square wave, sine wave, or any combination thereof. Electric current can be delivered all at once or, where the energy delivery mechanism 52 comprises two or more electrodes 66, electric current can be delivered to only one of the electrodes using a controller (not shown) and/or known complex practice, such as current steering.

The particular voltage, current, and frequency delivered to the energy delivery mechanism 52 may be varied as needed. For example, electric current can be delivered to the energy delivery mechanism 52 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Delivery of electric current to the energy delivery mechanism 52 stimulates the target nerve, i.e., causes the target nerve to increase the frequency of nerve impulses. Depending upon the anatomical structure(s) and/or other nerve pathways innervated by the target nerve, a measurable result indicative of the appropriate target nerve can be determined upon delivery of electric current. In a subject suffering from headache, for example, the measurable result may include some degree of pain relief. Alternatively, in a subject suffering from blepharospasm, the measurable result may include a reduction in uncontrolled blinking. If an appropriate measurable result is not observed upon delivery of electric current, the treatment probe 44 can be re-positioned, electric current again delivered to the energy delivery mechanism 52, and a measurable result then observed.

Figure 6:
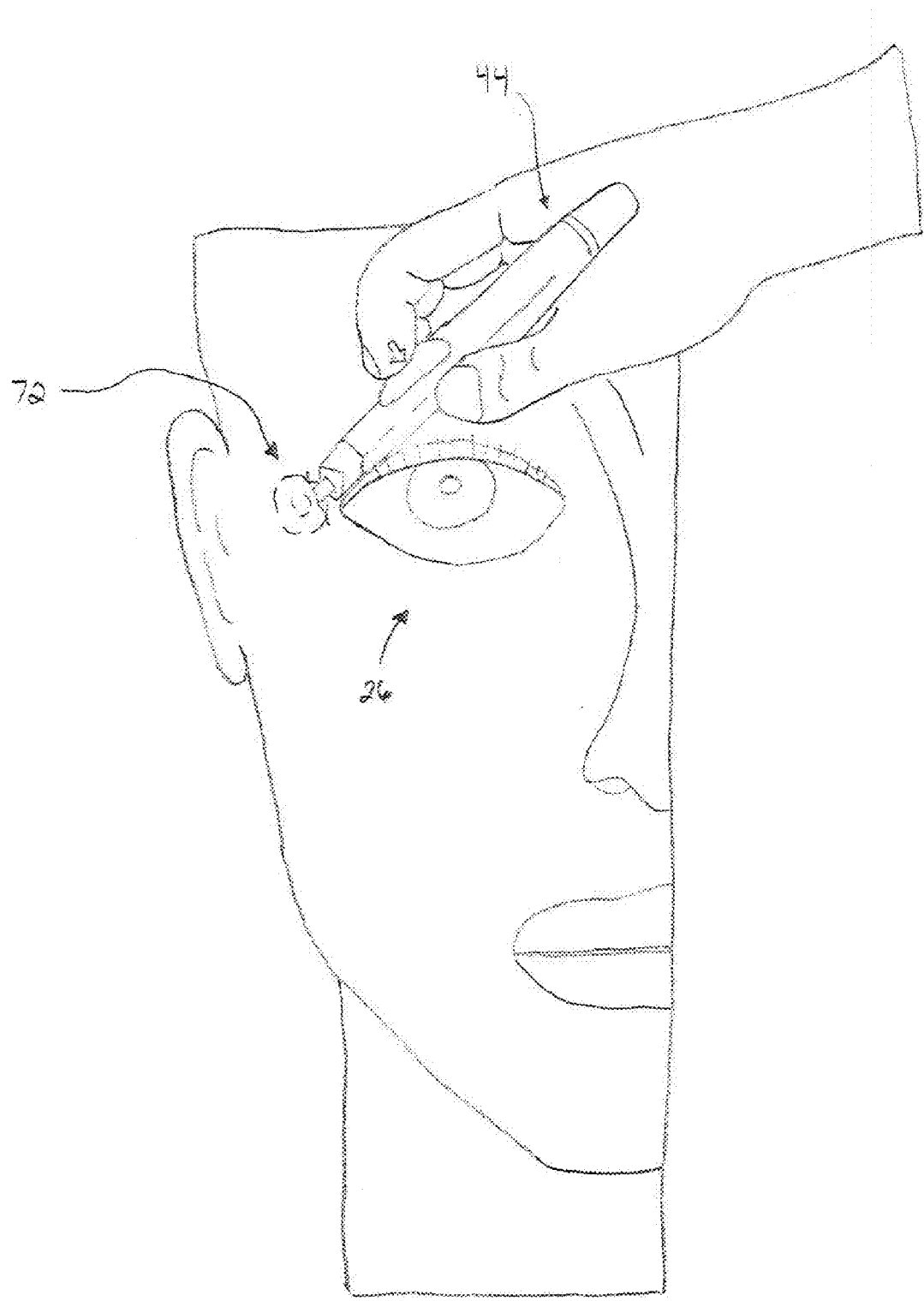

At 20, an appropriate volume of a tumescent fluid is injected into the tissue surrounding the target nerve. The tumescent fluid is selectively delivered to the tissue surrounding the target nerve via the channel 64 of the post member 58 (FIG. 6). The tumescent fluid can be stored in the treatment probe 44 or, alternatively, supplied from an external fluid source (not shown). The tumescent fluid can comprise any solution capable of protecting superficial tissue planes from inadvertent heat damage and enhancing electro-mechanical condition during delivery of electric current to the target nerve. For example, the tumescent fluid can comprise sterile water or an electrolyte solution (e.g., a physiologically normal saline solution).

Depending upon the particular neuromuscular defect being treated, the tumescent fluid can also include at least one pharmacological agent. Non-limiting examples of pharmacological agents can include anesthetic agents, such as lidocaine, marcaine, nesacaine, diprivan, novocaine, ketalar and xylocalne, vasoconstrictive agents, such as epinephrine, levarterenol, phenylephrine, athyladrianol and ephedrine, anti-inflammatory agents, such as free radical scavengers and anti-oxidants (e.g., superoxide dismutase, catalase, nitric oxide, mannitol, allopurinol, and dimethyl sulfoxide), NSAIDS (e.g., aspirin, acetaminophen, indomethacin and ibuprofen), steroidal agents (e.g., glucocorticoids and hormes), calcium channel blockers (e.g., nimodipine, nifedipine, verapamil and nicardipine), NMDA antagonists (e.g., magnesium sulfate and dextromethorphan), and neurotoxic agents, such as *Botulinum* toxin.

Figure 7A:
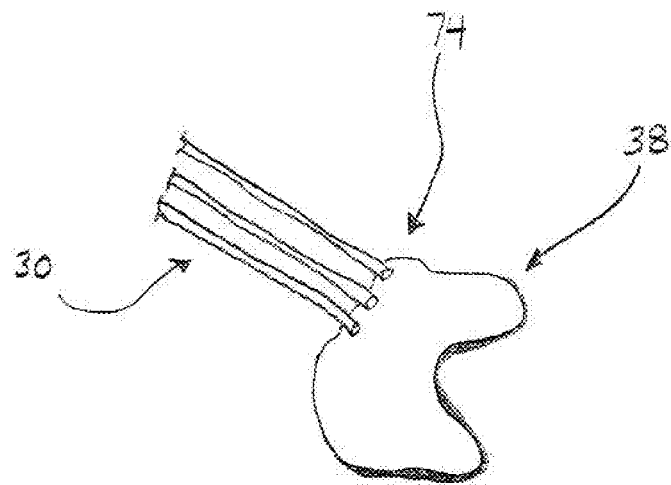

After an appropriate volume of tumescent fluid has been injected into the tissue surrounding the target nerve, the target nerve can be substantially ablated at 22. To substantially ablate the target nerve, the energy delivery mechanism 52 is positioned substantially adjacent a portion of the contractile chain comprising the target nerve. The contractile chain comprises nerve tissue (e.g., a neuron), a neuromuscular junction 74 (FIG. 7A) (which generally forms the interface between nerves and muscles), muscle tissue, and connective tissue. As shown in FIG. 7A, for example, the energy delivery mechanism 52 can be positioned substantially adjacent a neuromuscular junction 74.

Muscular movement is generally controlled by stimulation of a nerve. The motor unit of the neuromuscular system contains three components: motor neuron (spine), axon (spine to motor endplate), and innervated muscle fibers (endplate to muscle). Each muscle receives one or more supply nerves, and the supply nerve generally enters deep into the muscle surface near its origin where the muscle is relatively immobile. Often times, blood vessels can accompany the nerve to enter the muscle at the neurovascular hilum. Each nerve contains motor and sensory fibers, motor endplates, vascular smooth muscle cells, and various sensory endings and endings in fascia. When the nerve enters the muscle, it breaks off into a plexus running into the various layers of muscle epimysium, perimysium and endomysium, each terminating in several branches joining a muscle fiber at the motor endplate.

Substantially ablating one or more of these tissues may be sufficient to temporarily or permanently inhibit muscle contraction. Substantially ablating a target nerve may interrupt or disable nerve impulses by disrupting conductivity. Disruptions in nerve conductivity may be caused by eliminating or decreasing charge differences across plasma membranes, either mechanically or chemically, destroying Schwann cells that insulate the axonal processes, repeated injury/healing cycles timed to limited capacity for neuron regeneration, or a combination thereof.

The energy delivery mechanism 52 can be brought into direct or indirect contact with the target nerve. By "direct" it is meant that the energy delivery mechanism 52 is brought into physical contact with the target nerve. By "indirect" it is meant that the energy delivery mechanism 52 is positioned about the target nerve without directly contacting the target nerve, such that delivery of electric current to the energy delivery mechanism can modulate activity of the target nerve. Regardless of the specific component of the contractile chain which is substantially ablated, delivery of electric current to the target nerve can inhibit contraction of a muscle that would otherwise form or cause the neuromuscular defect.

Substantial ablation of the target nerve is accomplished when electric current is delivered to the energy delivery mechanism 52 via the power delivery source. The parameters for delivery of electric current to the energy delivery mechanism 52 can be identical or similar to the parameters described above. For example, electric current can be delivered to the energy delivery mechanism 52 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Figure 7B:
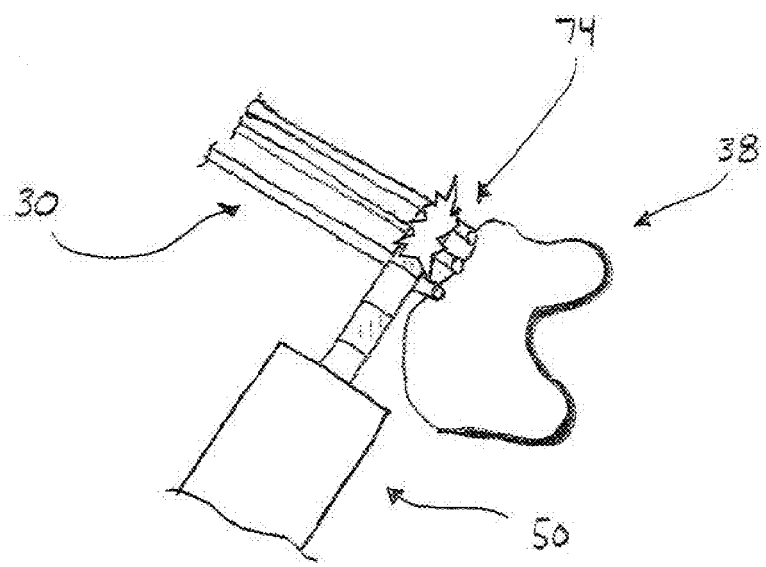
Figure 8:

As shown in FIG. 7B, delivery of electric current to the energy delivery mechanism 52 can substantially ablate a neuromuscular junction 74 comprising an end of a facial nerve 30 (or branch thereof) and the orbicularis palpebrarum muscle 38, for example. Such ablation may result in a short-term, long-term, or permanent inactivation of the muscle. Other long-lasting or permanent treatments may involve inducing apoptosis to remodel the tissue behavior with long-term changes in the cellular life and/or proliferation cycles.

Specific ablative approaches used to change the function of a nerve and its corresponding muscle(s) in a desired way, or for a desired time, may be induced by appropriate delivery of electric current to the energy delivery mechanism 52. Alternative ablative approaches that may be shorter in effect can include, for example, stunning of one or more components of contractile chain or inactivating one or more of the components. Ablative approaches that effectively block the release of, or response to, chemicals (e.g., neurotransmitters) along the contractile chain may also be sufficient to inhibit (e.g., temporarily or permanently) muscular contraction in response to signals transmitted along the neural pathways.

After substantially ablating the target nerve, the subject can be re-assessed to determine if the method 10 was effective in treating the neuromuscular defect. In a subject suffering from blepharospasm, for example, a medical practitioner or other health care professional can observe the subject for uncontrolled blinking. Depending upon the observed result, the method 10 can be repeated at 24. If the subject exhibits normal blinking, for example, no additional treatment may be needed. Where no additional treatment is needed, the incision 72 or entry point used to access the target nerve can be sutured or bandaged and the method 10 completed.

Although not illustrated in FIGS. 1-8, it should be appreciated that the method 10 can be targeted to any one or combination of the nerves or muscles identified in FIG. 3 to treat a variety of cosmetic defects other than blepharospasm. For example, the method 10 may be directed towards one or more of the levator palpebrae superioris, the frontalis, the levator labii, the corrugator supercilii 32, the zygomaticus minor, the zygomaticus major, the buccinator, and/or the temporalis. Treatments targeting contraction of the oticularis may help decrease crow's feet wrinkles, while treatments altering the function of the frontalis may alleviate wrinkles. Additionally, wrinkles of the chin may be mitigated by treatment of the mentali, and neck wrinkles may be improved by treatment of the platysm 36.

Other examples of muscles whose innervating nerve(s) may be substantially ablated to alleviate a cosmetic defect (or defects) can include the glabellar and procerus complex, the nasalis, the depressor anguli oris, the quadratus labii superioris and inferioris, the zygomaticus, the maxillae, the frontalis pars medialis, the frontalis pars lateralis, the levator palpebrae superioris, the orbicularis oculi pars orbitalis, the orbicularis oculi pars palpebralis, the levator labii superioris alaquae nasi, the levator labii superioris, the zygomaticus minor, the zygomaticus major, the levator anguli oris (a.k.a. caninus), the depressor anguli oris (a.k.a. triangularis), the depressor labii inferioris, the mentalis, the incisivii labii superioris, the incisivii labii inferioris, the risorius, the masseter, the internal pterygoid, the digastric, the maxillae, and the quadratus labii superioris and inferioris. Contraction of these and/or other muscles may be inhibited by targeting associated nervous tissue(s), connective tissue(s), nerve/muscle interface(s), blood supply, or a combination thereof.

From the above description of the invention, those skilled in the art will perceive improvements, changes and modifications. Such improvements, changes, and modifications are within the skill of the art and are intended to be covered by the appended claims.

Having described the invention, I claim:

1. A method for treating a neuromuscular defect in a subject, said method comprising the steps of:
   locating a target nerve;
   providing a treatment probe, the treatment probe comprising an elongated body member having a proximal end portion and a distal end portion, the distal end portion including an energy delivery mechanism for stimulating or ablating the target nerve, a monitoring mechanism, and a fluid aspiration and delivery mechanism;
   verifying that the target nerve is an appropriate target for ablation by stimulating and then monitoring the target nerve via the energy delivery mechanism and the monitoring mechanism, respectively;
   injecting a tumescent fluid into the tissue surrounding the target nerve; and
   delivering an electric current to the energy delivery mechanism to substantially ablate the target nerve;
   wherein said step of injecting a tumescent fluid into the tissue surrounding the target nerve protects superficial tissue planes from inadvertent heat damage and enhances electro-mechanical conduction during delivery of electric current to the target nerve;
   wherein said injecting step and said delivering step are performed using the same treatment probe;
   wherein delivery of the electric current temporarily or permanently inhibits muscle contraction;
   wherein the neurological movement disorder is selected from the group consisting of torticollis, blepharospasm, and uncontrolled grimacing.

2. The method of claim 1, wherein said step of locating a target nerve includes monitoring electrical activity of the target nerve via the monitoring mechanism.

3. The method of claim 2, wherein electromyographic monitoring is used to monitor the electrical activity of the target nerve.

4. The method of claim 1, wherein said step verifying that the target nerve is an appropriate target for ablation further comprises the steps of:
   applying a stimulation current to the target nerve via the energy delivery mechanism; and
   monitoring the subject for measurable result indicative of the appropriate target nerve.

5. The method of claim 4, wherein the measurable result indicative of the appropriate target nerve is at least one of an observable clinical result, an electromyographic signal or pattern, and a change in pain perception.

6. The method of claim 1, wherein said step of injecting a tumescent fluid into the tissue surrounding the target nerve further includes injecting a pharmacological agent into the tissue surrounding the target nerve.

7. The method of claim 6, wherein the pharmacological agent is selected from the group consisting of an anesthetic agent, an anti-inflammatory agent, an electrolyte solution, and a neurotoxic agent.

8. The method of claim 7, wherein the neurotoxic agent comprises Botulinum toxin.

\* \* \* \* \*